United States Patent [19]

Post

[11] Patent Number: 5,397,541
[45] Date of Patent: Mar. 14, 1995

[54] THIN FILM OXYGEN SENSOR

[75] Inventor: Michael L. Post, Orleans, Canada

[73] Assignee: National Research Council of Canada, Ottawa, Canada

[21] Appl. No.: 118,597

[22] Filed: Sep. 10, 1993

[51] Int. Cl.[6] .................. G01N 27/46; G01N 31/12
[52] U.S. Cl. .................................. 422/88; 422/98;
436/136; 436/137; 73/23.31; 73/23.32;
324/71.5; 338/34; 427/78; 427/126.3;
427/126.6; 204/412; 204/425
[58] Field of Search .................. 422/88, 90, 91, 98;
73/23.31, 23.32; 436/127, 136, 137; 324/71.5;
338/34; 427/77, 78, 100, 126.3, 126.6; 204/400,
407, 424, 426

[56] References Cited

U.S. PATENT DOCUMENTS

| | | | |
|---|---|---|---|
| 4,314,996 | 2/1982 | Sekido et al. | 422/98 |
| 4,608,232 | 8/1986 | Sunano et al. | 422/88 |
| 5,071,626 | 12/1991 | Tuller | 422/98 |

OTHER PUBLICATIONS

Post, M. L. et al. "Thin Films of Non–Stoichiometric Perovskites as Potential Oxygen Sensors." Sensors and Actuators B, vol. B13, No. 1–3, pp. 272–275 5, 1993.
Warner, J. D. et al. "Laser ablated high T sub c superconducting thin YBa2Cu3O(7−x) films on substrates suitable for microwave applications". Conference on Advances in material science and applications of high temperature superconductors. Greenbelt, Md. (USA) 2–6 Apr. 1990. NTIS, PC AU7/MF A02.
Lal, R et al. "Sensor Activity In Pulsed Laser Deposited and Ion Implanted Tin Oxide Films". Thin Solid Films, 1991, V206, N1-2, Dec. 10, pp. 88–93.

Primary Examiner—David A. Redding
Attorney, Agent, or Firm—Juliusz Szereszewski

[57] ABSTRACT

An oxygen sensor is based on a thin film of a compound oxide supported on a substrate such as quartz. The compound oxide has a general formula $ABO_{2.5+x}$, where A is an element of the lanthanum family, alkaline earth metal or their mixture, and B is a transition metal or a mixture of transition metals. X is a variable number, changing from about 0 to about 0.5 between the reversible oxygen-deplete and oxygen-rich forms of the oxide. In an elevated temperature and oxygen-containing atmosphere, the thin film can undergo reversible bulk oxidation resulting in a detectable change of its physical properties such as mass, optical transmissivity and electrical resistance.

14 Claims, 15 Drawing Sheets

THIN FILM OXYGEN SENSOR

FIELD OF THE INVENTION

This invention relates to oxygen sensors, and particularly to oxygen gas sensors having a layer of a compound oxide for detecting the concentration of oxygen in a surrounding atmosphere.

BACKGROUND OF THE INVENTION

The determination of the presence and/or quantity of oxygen in the gas phase is essential to the efficient operation of many processes and devices, particularly those involving combustion. Monitors currently in use provide analyses based on three principles: i) spectroscopy of the gas phase, ii) amperometric properties of certain types of electrolytic cells and iii) surface chemistry of gas adsorption onto selected solid materials (ie. Chemical Sensing). The first two involve expensive and bulky apparatus and can, with careful calibration, produce accurate analyses. The latter technique potentially provides cheap, small and robust devices, but a main deficiency of the analysis is non-specificity to the analyte gas, with consequent interferences with other gases present in the analyte gas stream.

U.S. Pat. No. 4,314,996 granted Feb. 9, 1982 to Sekido et al describes an oxygen sensor element comprising a substrate made of a compound oxide of the perovskite type and a pair of electrodes electrically connected to the substrate. The compound oxide has a formula $ABO_3$ in which A represents an element of the lanthanum family, an alkaline earth metal or a mixture thereof and B is a transition metal. The layer of the oxide is about 0.4 mm thick.

U.S. Pat. No. 4,608,232 issued Aug. 26, 1986 to Sunano et al describes a gas sensor which has an electrically insulating base, electrodes formed on the base, and a gas sensitive film formed on the surface of the base at a position where it detects oxygen gas. The gas sensitive film is a thermally sprayed film which is made of an oxide having a perovskite structure. The surface of the film is formed with fine cracks which increase the effective surface area and enhance the Speed of response of the sensor.

U.S. Pat. No. 5,071,626 issued Dec. 10, 1991 to Tuller describes an oxygen sensor having a sensing element of a copper oxide ceramic with perovskite related structure. The conductivity of the sensing element is a function of oxygen partial pressure. A preferred ceramic is the Y-Ba-Cu-O system. A suitable thickness of the sensor material is indicated to be 0.1–250 μm. The technique used to apply the film is spin-coating and pyrolysis. Alternatively, sputtering and vapor deposition is suggested, but no data or evidence for the sensing quality of the product which would be obtained by this route is provided in the disclosure.

There are many examples of metal oxides and doped analogues being used as sensor materials for the detection or analysis of a variety of volatile compounds. The mode of action of these devices depends upon surface chemistry of the sensing material, and the mechanism, which is of redox character, is not thoroughly understood. It is noted that some of the prior art sensors (see U.S. Pat. No. 4,608,232) react similarly to oxygen and to moisture (ie. cross interference). The reaction of the compound oxide of U.S. Pat. No. 4,314,996 is indicated to be $$LaCoO_3 \rightleftharpoons La_2O_3 + Co$$

The above-mentioned Sunano, Sekido and Tuller inventions use an approach described as thick film technology to produce the sensor surface, whereby a slurry of powdered perovskite and additives are sintered at high temperature onto a supporting substrate as a material which has ceramic physical properties.

SUMMARY OF THE INVENTION

It is an object of the invention to provide an oxygen sensor with increased oxygen specificity compared to prior art devices of similar type.

It is another object of the invention to provide an oxygen sensor relying, in addition to electrical resistance, on other physical property changes.

According to the invention, there is provided an oxygen sensor comprising, a substrate which is thermally stable at the temperature of deposition of a compound oxide as explained below and chemically stable towards that compound at that temperature, a thin layer of a compound oxide of the general formula $ABO_{2.5+x}$ supported on the substrate, wherein A is an element of the lanthanum family, an alkaline earth metal or a mixture thereof, B is a transition metal or a mixture of two or more transition metals, and x is a number which is variable between the oxygen deplete and oxygen saturated form of the compound oxide, the layer having a crystalline structure and being of a thickness enabling the compound oxide to undergo reversible bulk oxidation at an elevated temperature in an oxygen-containing atmosphere, thereby undergoing transition between the oxygen-rich and oxygen-deplete forms, and a means for detecting a change in physical properties of said layer, said change being a function of the varying bulk oxidation of the layer.

The physical properties that can be monitored to detect a change in bulk oxidation of the layer are, for instance, optical transmissivity, mass change, and electrical resistance.

The surface area of the layer is relatively low compared to the surface area characteristic to vapor deposition/sputtering or sintering techniques. Rather, it is in the order of the surface area characteristic of, or specific to, an epitaxial layer. Typically, the thickness of the layer is below 1 micrometer down to a few unit cells (ie. ∼3 nm).

Preferably, the substrate is sapphire but other non-conductive materials such as quartz, silicon or AT cut quartz can be used. The essential properties for the substrate are as follows. The substrate must be thermally stable at the operational temperature of the sensor (T∼400° C.), chemically stable towards the oxide applied and its surface prior to film deposition must be of a quality which permits the deposited material to adhere (physically bond), such that no spalling occurs upon thermal or chemical ($O_2$ deplete $\rightleftharpoons$ $O_2$ rich) cycling of the film.

BRIEF DESCRIPTION OF THE DRAWINGS

In the drawings,

FIG. 9b is a more detailed schematic representation of a part (chamber) of the apparatus of FIG. 9a;

DETAILED DESCRIPTION OF THE INVENTION

Figure 1:
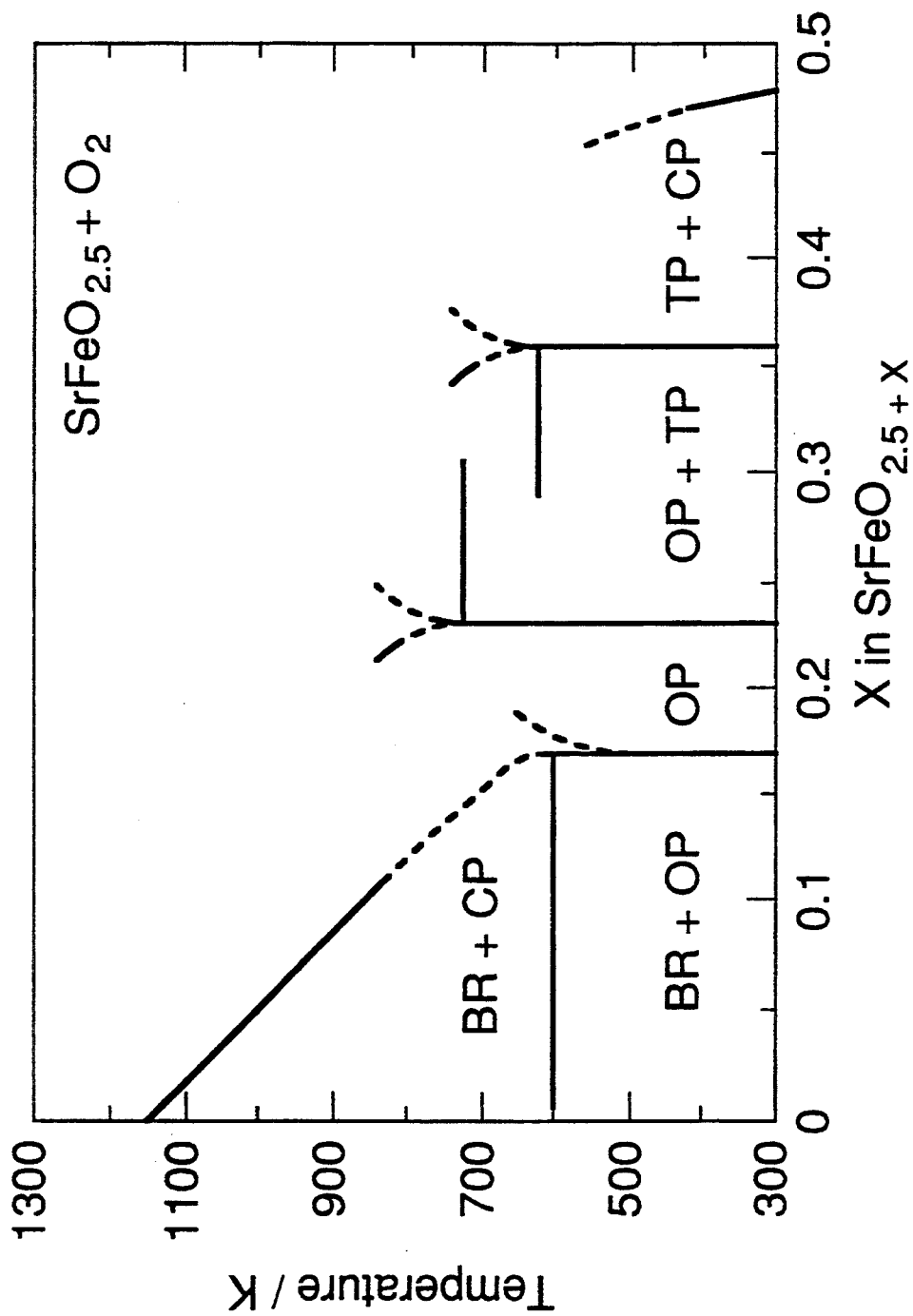
FIG. 1 shows the reduced phase diagram for the $SrFeO_{2.5+x} + O_2$ system.

The current invention addresses the specificity problem for the analysis of gaseous oxygen. The solid state chemistry of a particular class of non-stoichiometric oxides has been exploited to provide the sensing material for a chemical sensor device.

The difference between thick films and thin films will first be discussed for a better understanding of the invention. It is difficult to define the upper and lower limits of the thickness of the thin films of the invention as they depend on several factors.

Apart from the actual thickness, prior art thick films for sensor applications have intentionally high specific surface area resulting from a random association of irregular oxide particles, for instance obtained through sintering at high temperature. Note that, e.g., the U.S. Pat. No. 5,071,626 specifically claims the porosity of the ceramic layer. The surface is amenable to redox reactions, not necessitating the presence of oxygen, but only the presence of an oxidising or reducing species (ie. nonspecific reactions). Gaseous substances do not have to permeate the entire bulk of the material forming the layer since they take advantage of the relatively high porosity (surface area) of the film surface and react with the film at its surface through processes of adsorption. The active (sensor) surface of the metal oxide films have moieties which are not chemically representative of the bulk metal oxide material (as a result of exposure during or after preparation to redox species). The film exhibits at its surface MeOH (Me stands for metal) and MeH terminal moieties which react with a gas at the adsorption surface of the thick film. This results in a modification change of the electron path at the surface which results in a measurable change in surface electrical resistance. However, it should be borne in mind that any gas with a similar oxidation potential will react with the film giving a similar electronic resistance change as oxygen. Generally, the mechanism and relationship of analyte gas, the adsorption process and resulting resistance change is not well understood.

By comparison, thin films exhibit, importantly, a marked uniformity of the surface and an ordered crystallinity. What makes the difference in the structure compared with thick films is the technique of deposition. A recently developed method of pulsed laser ablation/deposition enables the deposition of highly uniform films with morphologies which can be either microcrystalline, oriented-crystalline, epitaxial or nearly-epitaxial layers; and of thickness ranging between a few tens of angstroms and a several thousand angstroms. The difference between these morphologies is determined by deposition parameters such as substrate and substrate temperature, laser power and fluence, deposition time and atmosphere composition & pressure during deposition.

The material of the film of the invention is structurally non-stoichiometric in oxygen and can undergo reversible reaction with oxygen between the upper and lower limiting forms, which are oxygen deplete and oxygen-saturated (oxygen-rich) forms. The material can also exist in any intermediate composition between the upper and lower oxygen content. The reaction is one of phase conversion in the bulk mass of the film, and not a surface reaction driven by redox potentials between analyte gas and the terminal moieties. There are two significant consequences to this bulk behaviour. Firstly, the bulk reaction results in very specific metal-oxygen bond formation / (breakage) and no other element will cause this particular reaction to occur; hence the reaction becomes specific to oxygen. Secondly, the thermodynamic principles of phase conversion of solid gas reactions can be exploited to select (enhance) the sensing properties/ranges to oxygen; particularly by choice of temperature of sensor operation which has the effect of extending the dynamic range of use for the sensor.

An advantage of the invention is in the relatively low thickness of the compound oxide film combined with the low specific surface area and the above-explained resulting bulk reaction mechanism. As a result, the changes in physical properties which accompany this bulk reaction are significantly large and hence a number of properties can be measured to provide a means of transduction to a measurable signal. For instance, a weight gain of the film resulting from the additional amount of oxygen reacted therewith, is measurable and can reach, according to our tests, up to 4% of the initial (oxygen-deplete) mass. The weight of the films is approximately 100–200 μg and the Δm is 4–8 μg, easily measured by BAW piezoelectric microbalance techniques, which have resolution in the ng range. Resistance changes, which our tests show to be larger than 30MΩ, indicate which ranges of $O_2$ compositions may be dynamic limits. The optical transmission and reflectance properties of the films are distinctly different when the films are at the limiting compositions.

The metal A can be Sr, La, Ba, other alkaline and rare earths or their mixture. B is preferably Fe, optionally substituted partially by Ti, V, Cr, Mn, Co, Ni, Cu and other transition elements. It is important that the major component represented by metal B (Fe) be stable in two or more oxidation states within the structure of the compound oxide. Also, it is important that the total molar ratio of elements A to elements B (with their partial substituents, where applicable) should not be different from unity and that the resulting structures are isomorphous, or closely isomorphous, with the $SrFeO_{2.5+x}$, so that the end member phases are brown-millerite or at least orthorhombic distorted perovskite (low x) and higher symmetry perovskite (high x). Provided that the above is satisfied, the valency/oxidation state of the substituent elements need not be the same as the valency of the basic elements A and B since the structures can tolerate some distortion. Up to about 10% substitution is satisfactory, at some higher substitution levels, non-stoichiometric compound oxides of the invention cannot be obtained. In other words, precise metal and O stoichiometry appears important for the film to behave as a bulk sensor. X-ray diffraction spectra allow identification and confirmation that the desired structure is achieved by a compound oxide. Table 1, annexed to the disclosure, shows suitable compound oxides and their X-ray diffraction spectra.

In addition to the strict structural requirements, the width (span) of the non-stoichiometry (x) must be large enough to provide a bulk composition range. This property has been measured by isothermal gas absorption techniques, and the values are reported in Table 2, annexed at the end of the disclosure. In these tests, conducted to validate the invention, $SrFeO_{2.5+x}$ exhibited the largest span of x, from 0 to about 0.45. Other compounds tested had x ranging from about 0.2 to about 0.4. While it is also desirable to identify the compounds with the best kinetics of the reverse oxidation, $SrFeO_{2.5+x}$ appears to be the preferable compound oxide for the purpose of the invention.

EXPERIMENTAL

A. Preparation of the $ABO_{2.5+x}$ materials

Bulk powdered samples of $SrFeO_{2.5+x}$ were prepared by sintering stoichiometric mixtures of $SrCO_3$ and $Fe_2O_3$ at temperatures up to T=1530 K. $Sr_{0.9}La_{0.1}FeO_{2.5+x}$ was prepared similarly, with $La_2O_3$ substituting $SrCO_3$ in the appropriate stoichiometric ratio. For the materials $SrFe_{0.9}B_{0.1}O_{2.5+x}$, the same approach was taken to achieve the desired stoichiometry by substituting with the oxide of the B element. All starting materials were Johnson-Matthey, Puratronic Grade 99.99% or 99.999% purity. Phase and elemental purity of the products were confirmed by x-ray diffraction and ICP-mass spectrometry, respectively. X-ray data were obtained on a Scintag P2000 diffractometer, operating with $\theta$—$\theta$ geometry and with graphite monochromated Cu-K$_\alpha$ radiation. The thermodynamics for oxygen reaction for all the systems $ABO_{2.5+x}$, $AA'BO_{2.5+x}$, $ABB'O_{2.5+x}$, with gaseous oxygen were determined at 520 K. by measuring the pressure vs composition,(p-x),isotherms. These data were collected by using a stainless steel reactor (for sample containment) and a manifold for gas manipulations. Gas titrations were done in a high precision experiment using volumetric calculations based upon calibrated volumes and accurate oxygen pressure, p($O_2$), values. Composition uncertainties with this apparatus were better than ±0.01 in x. In this manner, the phase co-existence regions were identified, as were the $O_2$ pressures necessary to achieve a given composition, x. Additional data were obtained at other temperatures, and reversibility of the $O_2$ reaction was demonstrated at all temperatures by removing small quantities of $O_2$, ($\delta x$), by using reverse gas titration, in a desorption mode from the samples which had reached high $O_2$ content (ie. oxygen rich).

Figure 1A:
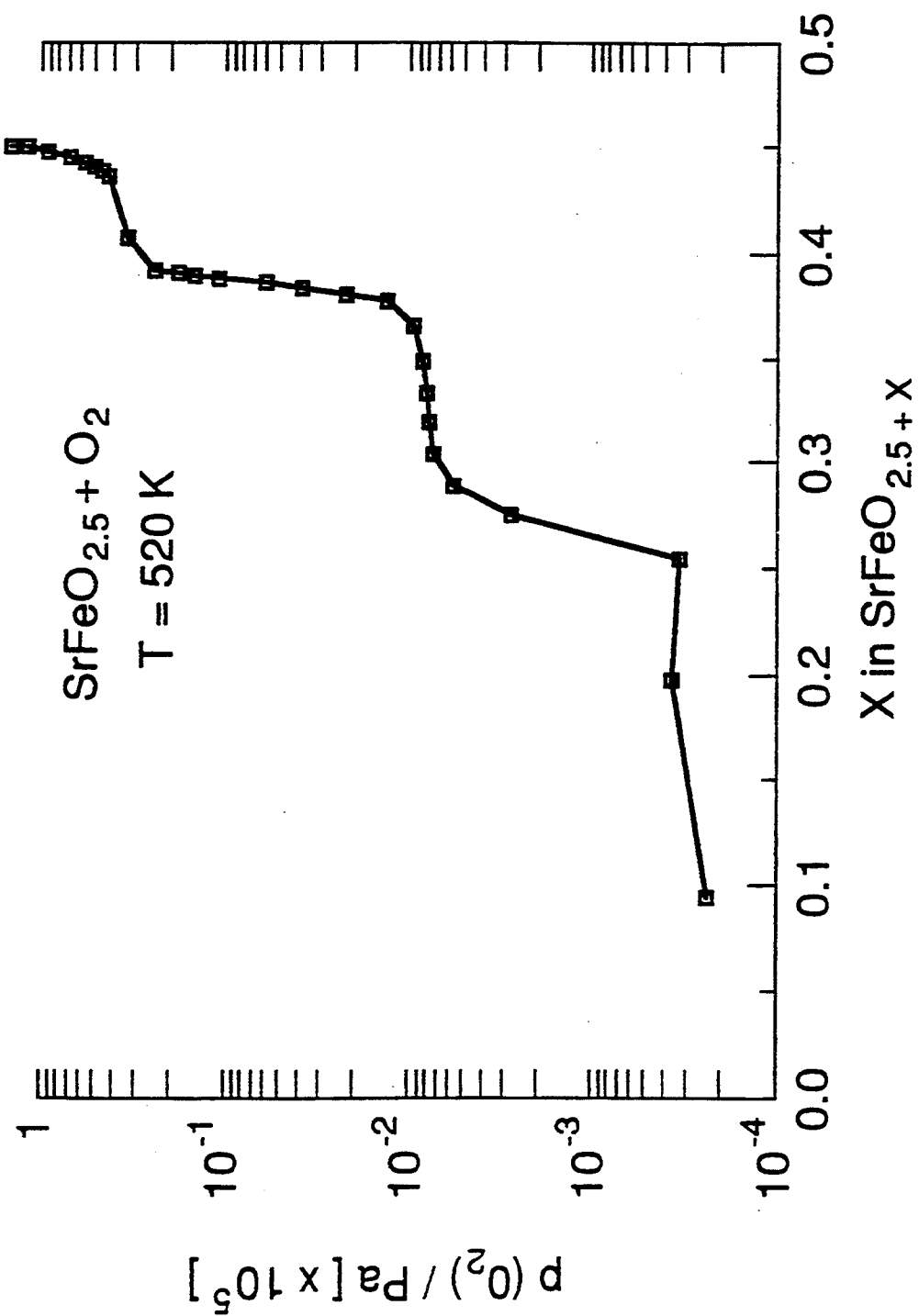
FIG. 1a shows p-x isotherm for the above system at 520 K.
Figure 2:
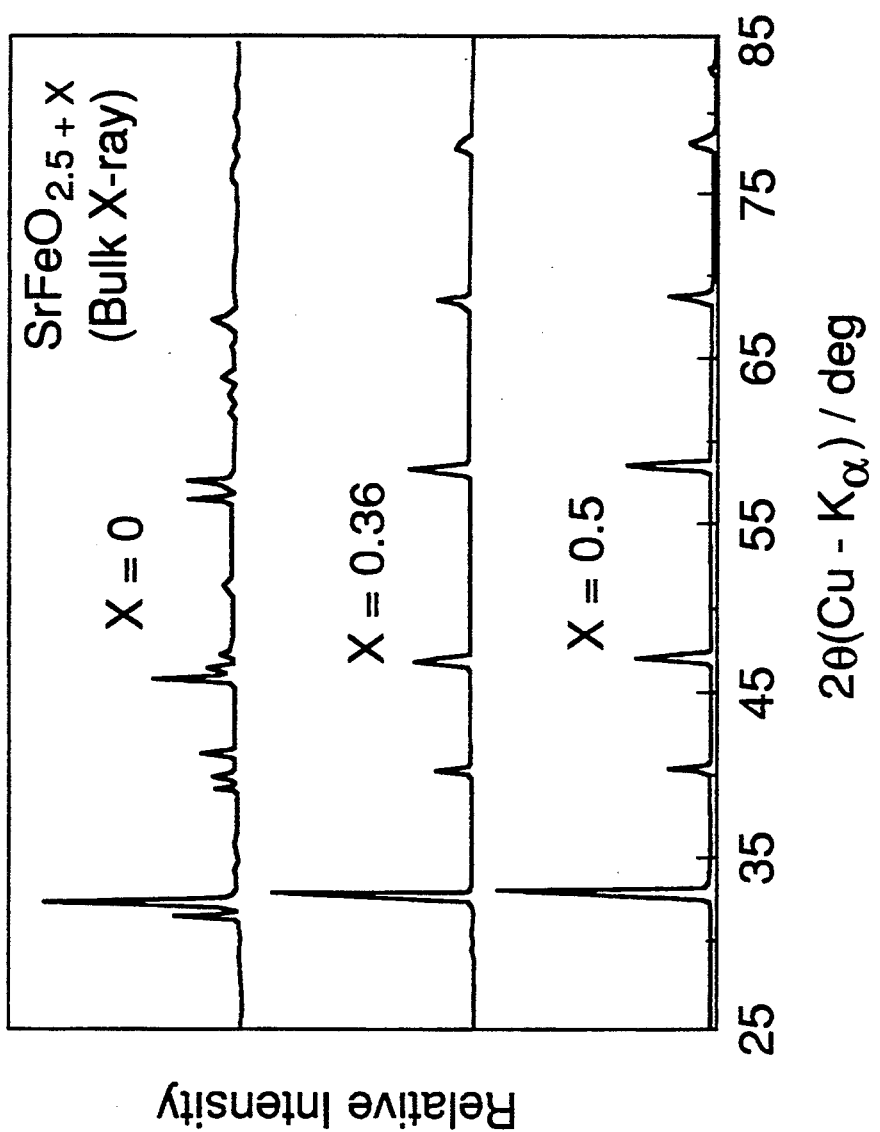
FIG. 2 shows X-ray diffraction spectra of bulk powder samples of $SrFeO_{2.5+x}$ taken with monochromated $Cu\text{-}K_\alpha$ radiation.

Data obtained in p-x isotherms were used to show phase boundaries. For instance, FIG. 1a illustrates a p-x isotherm for the $SrFeO_{2.5+x}+O_2$ system at T=520 K., and FIG. 1 shows a reduced phase diagram for the $SrFeO_{2.5+x}+O_2$ system. The results confirm the existence of the four phases of this compound oxide in the range $0 \leq x \leq 0.5$. FIG. 1 illustrates the phase existence ranges for the orthorhombic-brownmillerite (BR), orthorhombic-perovskite (OP), tetragonal-perovskite (TP) and cubic-perovskite (CP) forms. X-ray data for $SrFeO_{2.5+x}$ in bulk powder form, for x=0, 0.36 and ~0.5 are shown in FIG. 2, and these correspond to BR, TP and CP structures, respectively. Hence for the $SrFeO_{2.5+x}$ system, oxygen vacancy ordering results in the existence of four phases in the range of x from 0 to about 0.45, and with T<750 K. and p($O_2$)<0.2 MPa.

B. Preparation of Sintered $ABO_{2.5+x}$

The powdered perovskite is not suitable for forming thin films. The preferred form is a sintered pellet which can be used as a target in the laser ablation step, for which the description follows in section C. About 2 g of $SrFeO_{2.5+x}$ are isostatically pressed to 10 tonnes at ambient temperature. The resulting pellet is then sintered in a high temperature annealing step. By using an oxygen containing atmosphere in this step, well sintered pellets of oxygen rich $SrFeO_{\sim 3}$ are obtained. In a non-oxygen containing atmosphere, $SrFeO_{2.5}$ is prepared. To create an oxygen deplete target (x=0) a pellet was annealed in an Ar stream at 1525 K. for 12 hours, then cooled 6 hours in Ar. To create an oxygen rich target (x≈0.5), a pellet was annealed in an oxygen stream at 1525 K. for 12 hours, then cooled over 6 hrs in oxygen.

C. Pulsed Laser Ablation-Deposition of $SrFeO_{2.5}$

Figure 3:
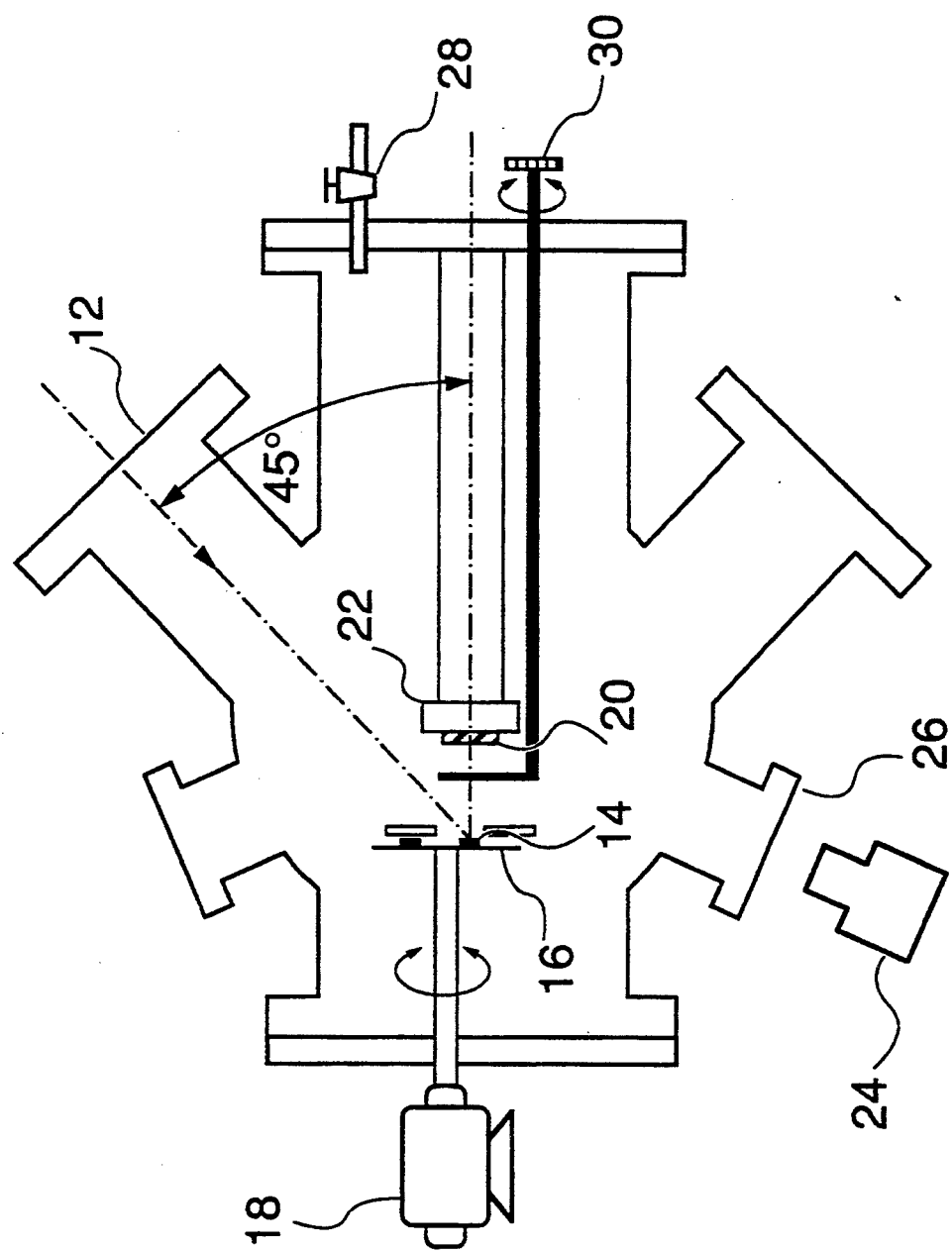
FIG. 3 is a schematic view of a laser ablation apparatus for producing thin films of the invention.

FIG. 3 shows a schematic of the deposition system. An excimer laser (KrF; $\lambda$=248 nm), not shown, pulsed at 10 Hz and with its output focused to give a fluence of up to 3.9 Jcm$^{-2}$ at the target, is used as an energy source. The laser beam is directed through a quartz window 12 onto a target 14 which is mounted on a rotating target holder, a copper plate 16. The holder 16 is rotated through a stepper motor 18. Prior to initiating deposition onto the substrate 20, the target 14 is cleaned by laser pulses for 20 s with the shutter 30 positioned to obscure the substrate. The shutter 30 is then opened, and the thermal ablation of the laser beam causes the target particles to form a plasma and deposit on a substrate 20, at a distance of 3–6 cm, mounted on a carrier with substrate heater 22. The substrate is heated, the temperature being controlled with a 100 W power supply and monitored with a thermocouple (not shown) in contact with a resistance heater and/or a pyrometer 24 through a window 26. Other details of the equipment and deposition parameters are reported by B. W. Sanders and M. L. Post, Ext. Abstracts 182nd Elec. Chem. Soc. Meeting, 92-2, 1024 (1992).

Films were grown from targets made as prepared above (section B) as sintered pellets of composition $SrFeO_{2.5+x}$ with x=0 and x≈0.5, in atmospheres ranging from vacuum [p($O_2$)<1.3×10$^{-4}$Pa] to p($O_2$)~40 Pa. The oxygen pressure was controlled by the micrometer leak valve 28. The power density incident upon the target was selected in the range 0.69 to 3.85 $J/cm^2$. Films were deposited for 20 min on ($1\bar{1}02$) oriented sapphire, optically polished sapphire, polished quartz or on gold coated AT cut quartz substrates. Sometimes the sapphire substrates were first coated in situ with an ablated thin film of cerium dioxide (from a target of $CeO_2$, prepared in an analogous manner to the perovskites), before the perovskite layer was deposited. The resulting film thickness was less than 300 nm. Deposition temperatures of 300 to 1130 K. were employed and monitored as indicated above. The atmosphere during ablation was selected from vacuum ($1.3 \times 10^{-4}$ Pa) to 40 Pa of oxygen. Two cooling atmospheres were used: vacuum and 53.3 kPa oxygen. Thin films of $SrFeO_{2.5+x}$ and $Sr_{0.9}La_{0.1}FeO_{2.5+x}$ were deposited.

D. Thin Films of $ABO_{2.5+x}$

Figure 4:
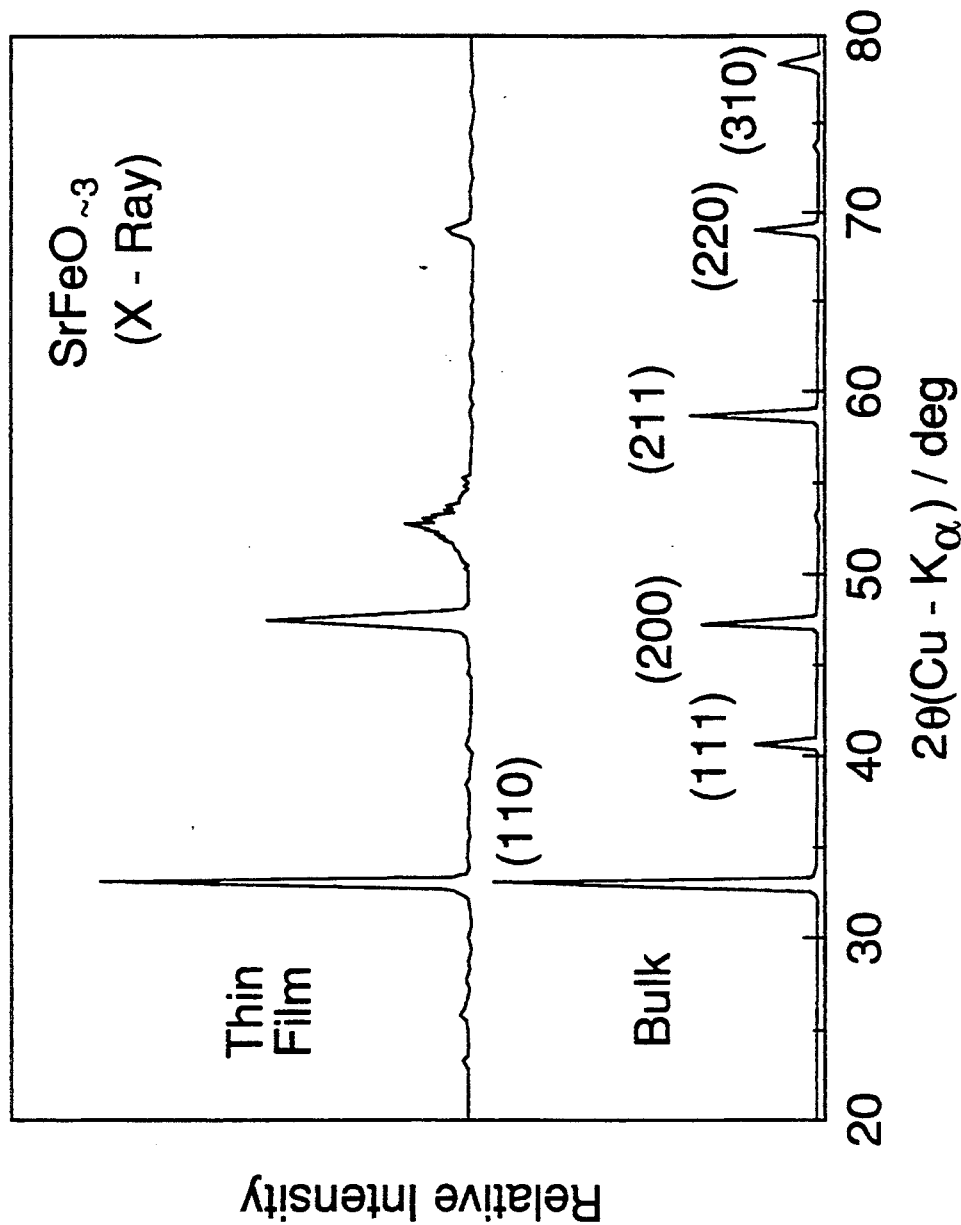
FIG. 4 shows the x-ray diffraction spectra of $SrFeO_{\sim 3}$ as powder and thin film on $(1\bar{1}02)$ oriented sapphire.

The deposited films had a thickness between 100 to 300 nm as measured by patterning the film and using a precision stylus probe (Dektak). X-ray diffraction spectra were used to identify the phase present in films prepared with different oxygen compositions. Substrate temperature has a large effect on film crystallinity. At temperatures below 770 K. no peaks were evident in the x-ray diffraction spectra of any film. At temperatures of 910 K. the best preferentially oriented polycrystalline (or perhaps even epitaxial) films were grown in vacuum from the oxygen deplete target. These films had the BR (brownmillerite structure) and showed two major peaks in the x-ray spectra, these indexed as (200) and (002). At 1000 K. excellent quality films were prepared in 26 Pa oxygen from the oxygen rich target. These films had a CP (cubic perovskite) structure and were oriented (110) and (100), FIG. 4. [The cubic (110) plane is equivalent to the (200) and (002) of the orthorhombic brownmillerite structure. In the cubic structure, the direction of the unit cell axes are redefined and the {200} set becomes equivalent to {110}]. Substrate temperatures above these values (for either target) led to the growth of additional orientations. The addition of a thin cerium dioxide layer between the film and the sapphire resulted in a higher degree of oriented crystallinity in the temperature range 770 K. to 910 K.

The atmosphere during cool-down had a greater effect on the film oxygen content than the growth atmosphere. Films deposited and cooled in vacuum were transparent and yellow in color. Films grown in 26 or 40 Pa oxygen and cooled in the same atmosphere were less transparent and brown in color. Films deposited in vacuum but cooled in oxygen became progressively darker and less transparent as the cooling pressure was increased. There was also a shift in the crystal structure from orthorhombic brownmillerite to cubic perovskite. Films grown in 26 to 40 Pa oxygen but cooled in vacuum showed the opposite effect—a change in crystal structure from cubic perovskite to brownmillerite and an appearance change to transparent yellow. By cooling in oxygen at a pressure of 53.3 kPa (for films grown in either oxygen or vacuum) the films became very reflective and appeared metallic. The peaks in the x-ray diffraction spectrum intensified.

E. Batch $O_2$ treatment of thin $ABO_{2.5+x}$ films

Structural Changes

Figure 5:
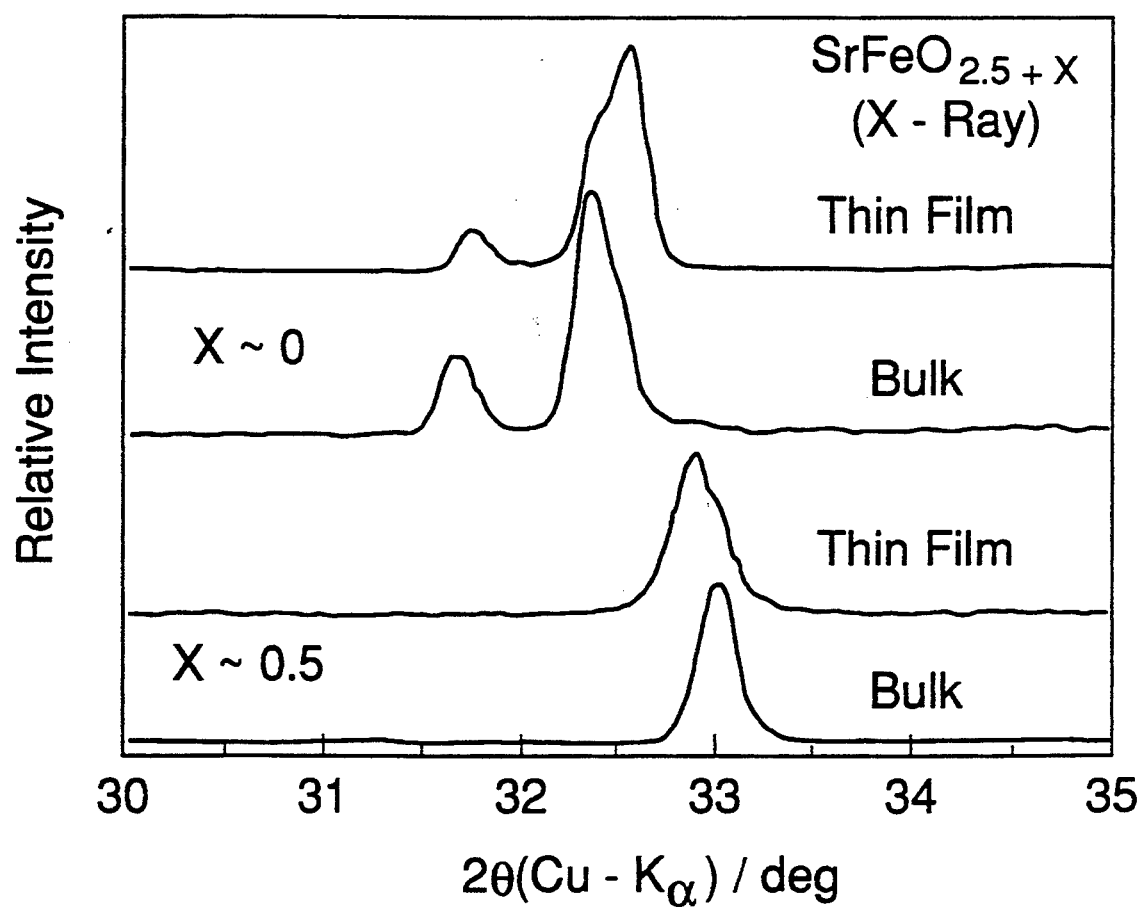
FIG. 5 illustrates X-ray diffraction spectra of the (110) region for $SrFeO_{2.5+x}$ for both powder and thin film samples.
Figure 6:
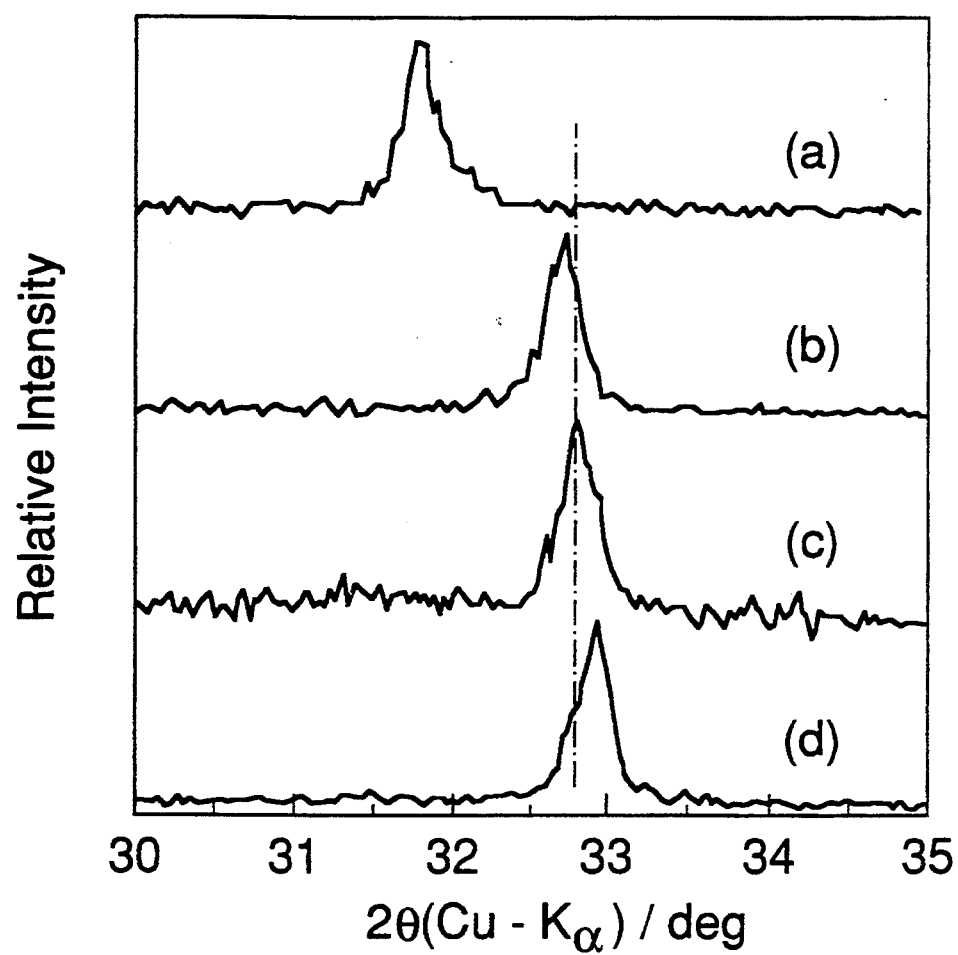
FIG. 6 shows X-ray diffraction spectra for thin-films of $Sr_{0.9}La_{0.1}FeO_{\sim 2.5+x}$.

Following deposition, the films were also exposed to oxygen at different temperatures and pressures, $p(O_2)$, in a batch process, using an apparatus constructed from stainless steel and equipped to facilitate gas manipulations between a manifold and the sample. Products were cooled to ambient temperature for further investigation. X-ray data obtained (FIG. 5) from the products showed that the bulk of the oriented film material was reacting with $O_2$, as shown by comparing the spectra with those for the powder $ABO_{2.5+x}$. In FIG. 5, the upper pair of curves indicates the $O_2$ deplete BR structure and the lower pair indicates the $O_2$ rich CP form. Reversibility between these forms has been demonstrated. Films which are either deposited and then cooled in oxygen with $p(O_2) > 0.05$ MPa, or post-treated in oxygen at $T > 420$ K. and then cooled, exhibit the oxygen-rich ($x > 0.45$) form, identified as the cubic-perovskite modification, as described above. The other phases have intermediate stoichiometry, and the structure passes through tetragonal and orthorhombic distorted-perovskite modifications as x decreases. The x-ray spectra of the four compositions of a film of $Sr_{0.9}La_{0.1}FeO_{\sim 2.5+x}$ are shown in FIG. 6, where the reflection shown is (110) based on the CP structure. The broken line at $2\theta \approx 32.8°$ is a guide to show the peak shifts of the (110) reflection. The $p(O_2)$ values for film preparation in FIG. 5 were: a) $1.3 \times 10^{-4}$ Pa, b) 3.5 Pa, c) 30 Pa, d) 101 kPa. The structure at the upper phase limit ($x \approx 0.5$) is cubic and analogous to that for $SrFeO_{\sim 3}$. At the lower phase limit, $Sr_{0.9}La_{0.1}FeO_{\sim 2.5}$ appears in a form best described as an orthorhombic-perovskite modification, and the corresponding x-ray diffraction spectrum (FIG. 6) does not exhibit the peak splitting expected for the brownmillerite structure.

Optical property changes

In the bulk powder form, the color of the two materials is black and brown for the oxygen-rich and oxygen deplete compositions, respectively. As thin films, the difference is also distinct: for $x \approx 0.5$ the product is metallic in appearance and also reflective; for $x \approx 0$ the product is pale yellow and transparent. Transmittance spectra for the treated films on transparent substrates were obtained at ambient temperatures over the wavelength range $200 \leq \lambda \leq 800$ nm with an HP8450A or Cary 1E spectrophotometer. Spectra for the films were referenced to uncoated ($1\bar{1}02$) sapphire. The absorption edge shifts to longer wavelengths as the oxygen content in the film increases (from approximately 350 nm for the oxygen deplete film to 850 nm for the oxygen-rich film). The films become more absorbing at all wavelengths as the oxygen content increases. Most of the absorbance changes occur in the oxygen pressure range 0 to 20 Pa. It is possible that some of this increase in absorbance is due to the increased reflectivity of the films with the increase in oxygen content.

Figure 7:
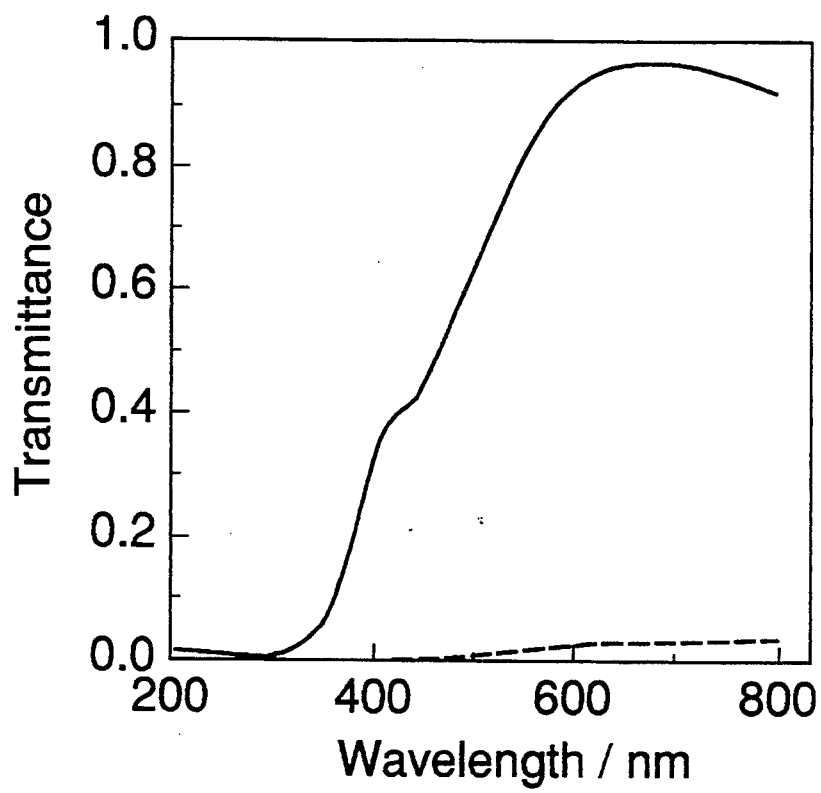
FIG. 7 presents transmission spectra in the UV-VIS region for thin films of $SrFeO_{2.5+x}$ at the stoichiometric limits.
Figure 7A:
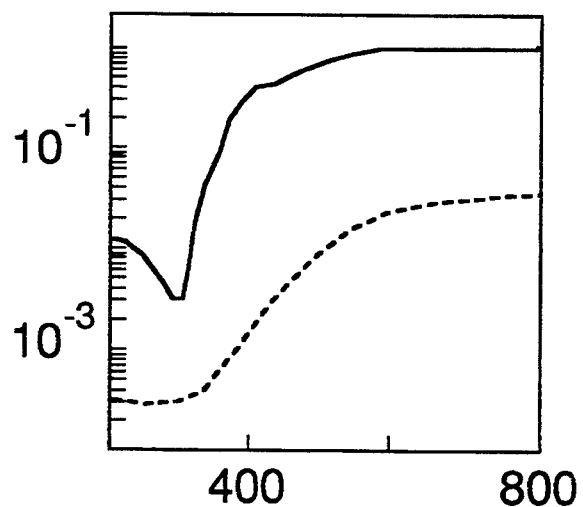
FIG. 7a presents the same data as FIG. 7 but plotted with a logarithmic axis.
Figure 8:
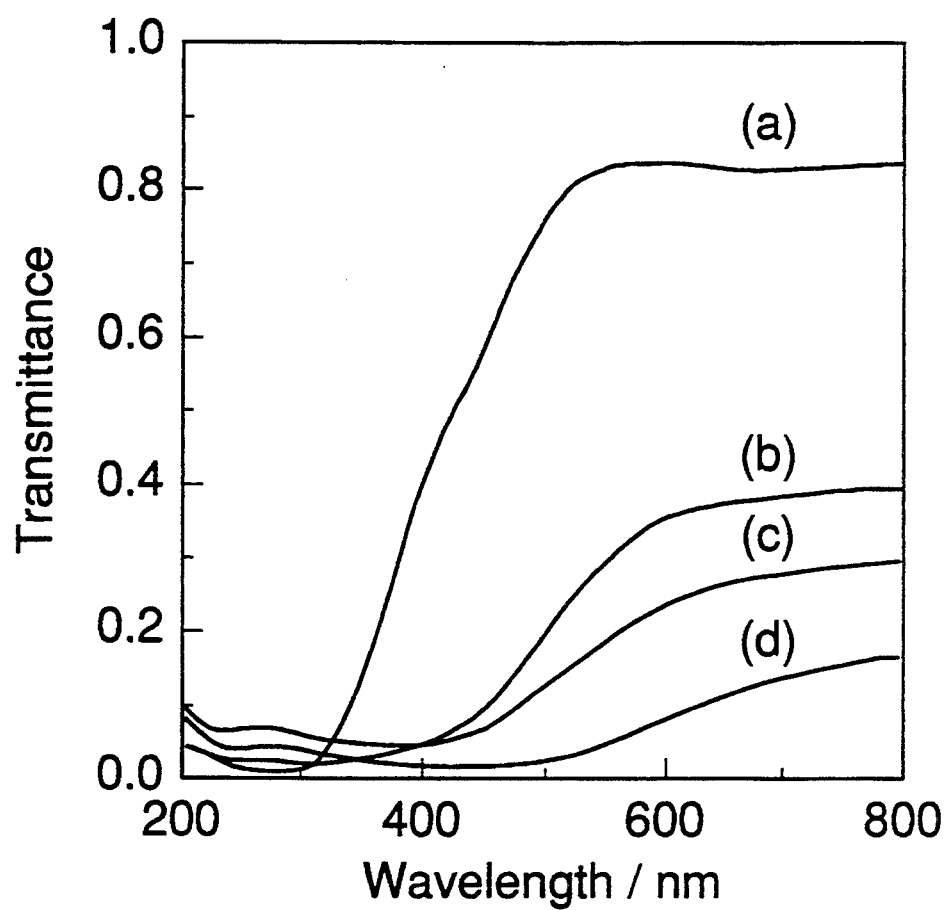
FIG. 8 shows transmittance spectra in the UV-VIS region for thin films of $Sr_{0.9}La_{0.1}FeO_{\sim 2.5+x}$.

FIG. 7 shows the uv-vis spectra of the $SrFeO_{2.5+x}$ films at each composition limit, and where the upper (full) curve has $x \approx 0$ in the BR form, and the lower (broken) curve has $x \approx 0.5$ in the CP form. FIG. 7a views same data as FIG. 7 plotted with a logarithmic axis. For both compositions the transmittance is highest over most of the visible portion of the spectrum, decreasing by a factor of about $10^2$ in the ultraviolet. The transmittance for $SrFeO_{\sim 3}$ is lower than that for $SrFeO_{2.5+x}$ for all wavelengths, with a maximum difference of greater than two orders of magnitude for $\lambda \approx 400$ nm. FIG. 8 shows uv-vis spectra for thin films of $Sr_{0.9}La_{0.1}FeO_{\sim 2.5+x}$ which were obtained by using different T and $p(O_2)$ treatments, as for FIG. 6. The data labelled (a)-(d) are from films having x values of 0, 0.39, 0.45 and 0.5, respectively. The overall features of the spectra compare with those for $SrFeO_{2.5+x}$, but, for all wavelengths, the transmittance at high x is an order of magnitude larger. There is an increase in transmittance with decreasing x, and the largest changes are observed for those films exposed to oxygen through the pressure range $10^{-4} < p(O_2) < 10 Pa$. The wavelength over which the largest difference in transmittance occurs for both the materials which have been studied, is $400 < \lambda < 550$ nm, which corresponds to the position of the absorption edge in these systems. By judicious choice of the optimum conditions of $\lambda$ and T the transmittance difference can be maximised for a selected oxygen pressure range.

F. In Situ thin film measurements for $SrFeO_{2.5+x}$

Figure 9A:
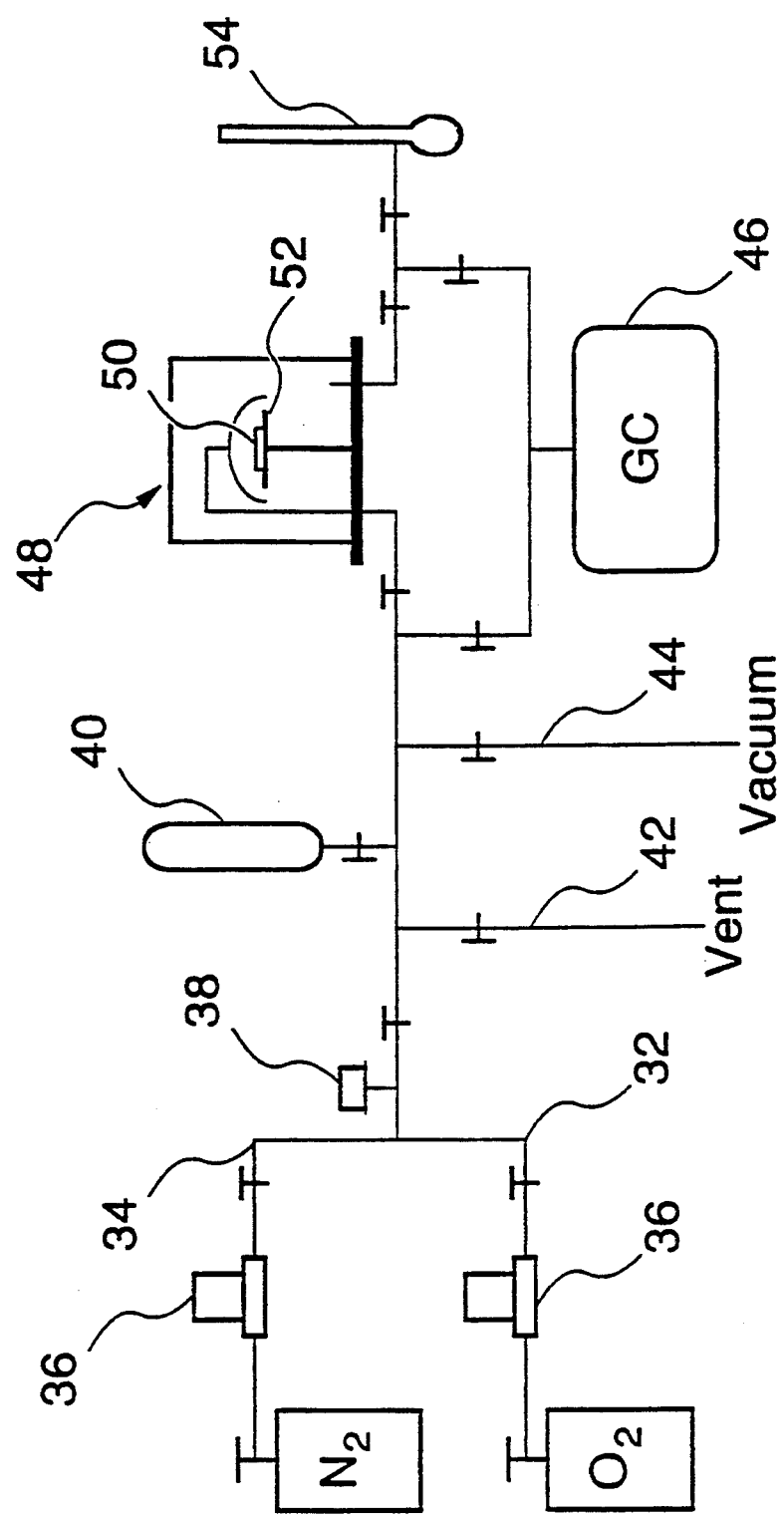
FIG. 9a is a schematic of the thin film resistance measurement apparatus.
Figure 9B:
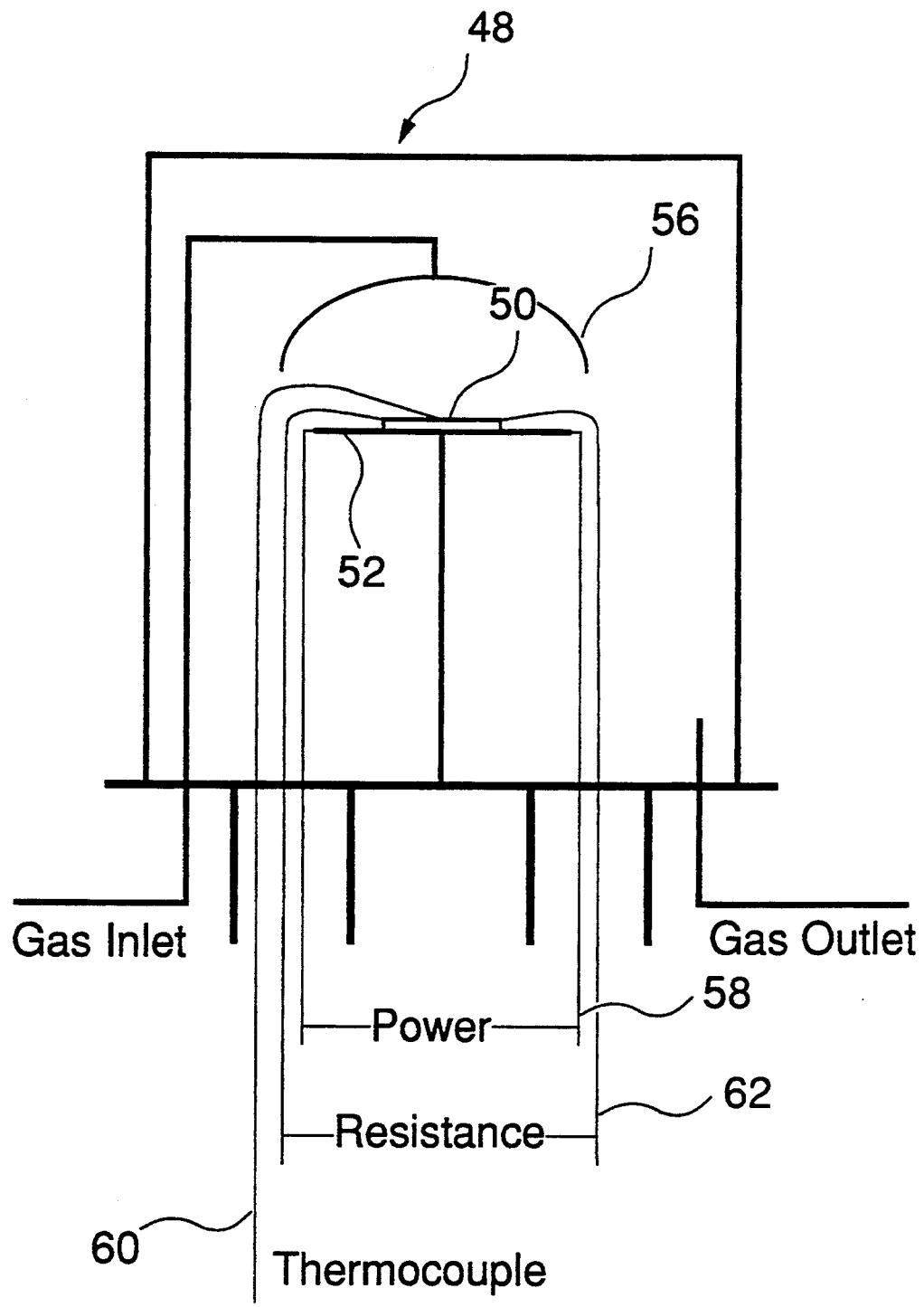

When exposed to oxygen at moderate temperatures (520–700 K.), the films undergo the same chemical reaction as shown for the bulk powder materials (section A). That is, the films are reacting through the complete thickness of the material which is deposited upon the substrate. Consequently, some large changes in physical properties accompany the bulk chemical changes. Of these physical properties, those that can be measured for use in sensor transduction in situ are optical, mass and electrical. The in situ measurements are made by combining a gas mixing/delivery system with an apparatus to achieve film exposure to the gas mixture at elevated temperature. Such a combined system is shown in FIG. 9a, where two gases are metered through mass flow controllers 36 into lines 32 and 34 for mixing at a pressure monitored with a transducer 38 and for intermediate storage in a containment vessel 40. The mixing system can be vented at 42 or evacuated at 44. The composition of the gas mixture is determined with a gas chromatograph 46 prior to it being admitted to the chamber 48, which contains the film 50 under test, mounted on a heater 52. The gas flow rate is measured with a meter 54. FIG. 9b, illustrates the chamber 48 details, with the film 50 on the heater 52 and the gas delivery dispersed over the film through umbrella 56. The power to the heater is through connections 58, and the temperature of the film is monitored with a thermocouple 60. The resistance of the film is measured with connections 62. Listed below are some examples of the use of systems based on this type, with heated films which are exposed to a gas stream consisting of a mixture of $O_2$ and $N_2$ at various concentrations.

EXAMPLES

Example 1

Figure 10:
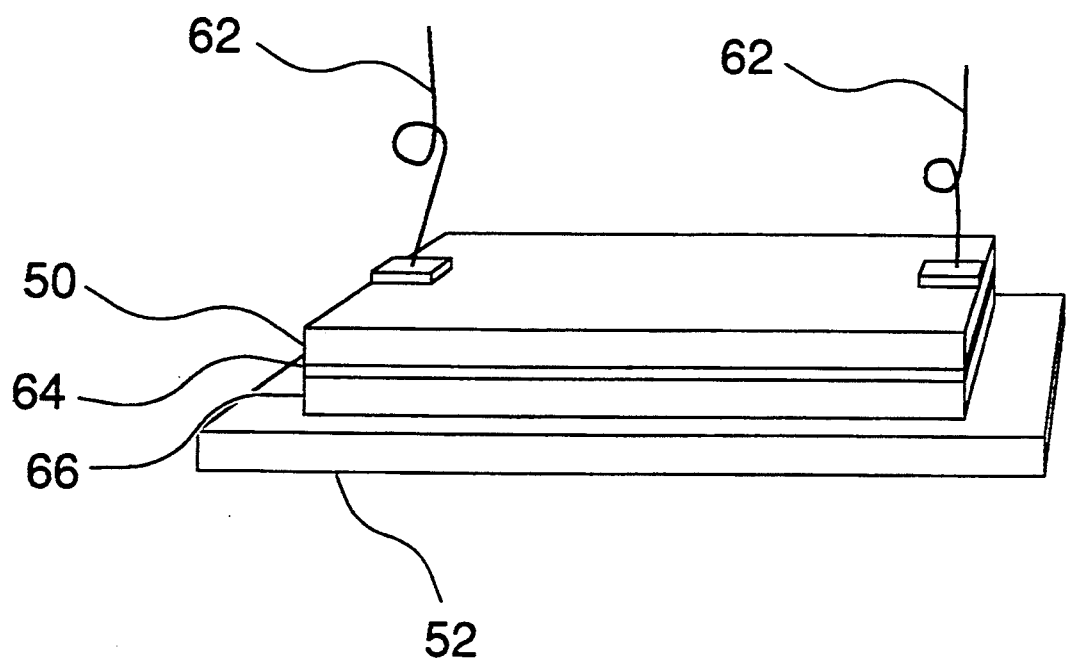
FIG. 10 shows an exemplary thin film oxygen sensor of the invention.
Figure 11:
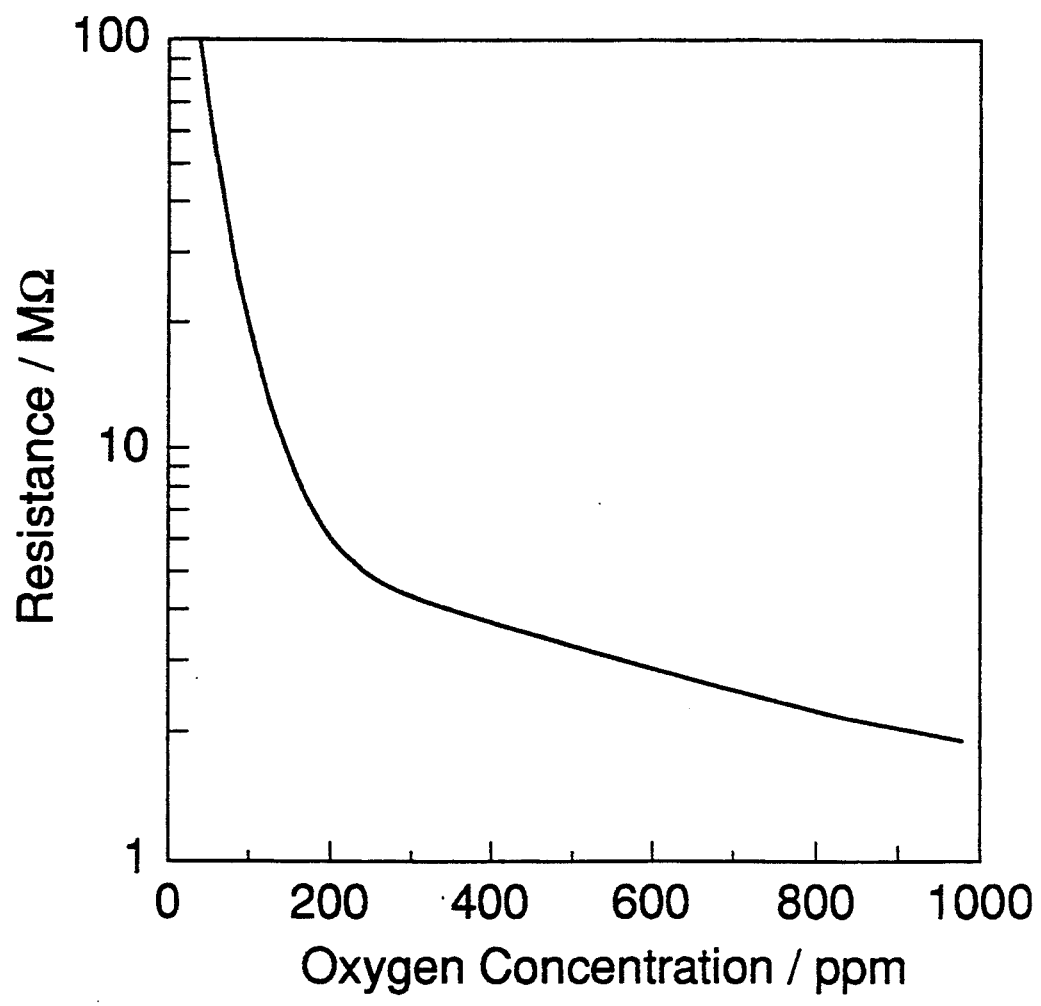
FIG. 11 is a graph showing the relationship between electrical resistance of a thin film oxygen sensor of the invention and the oxygen concentration.

A film of $SrFeO_{2.5+x}$ was deposited on $(1\bar{1}02)$ sapphire. To the film, electrical connection was made by bonding thin (0.005") gold wires 62 to evaporated gold pads on the film 50, assembled as shown in FIG. 10, with a $CeO_2$ buffer layer 64 on the non-conducting substrate 66 (sapphire). The assembly was attached to a ceramic plate heater 52. The resistance of the film was monitored by connecting the wires 62 to an external measurement circuit. The temperature of the $SrFeO_{2.5+x}$ film was controlled at 670 K. by mounting the film on a resistive heater with a PC controller. The resistance change when exposed to changing $O_2/N_2$ mixtures is shown in FIG. 11. The resistance changes are large for gas mixtures with compositions of $O_2 < 1000$ ppm. At higher concentrations of $O_2$, the coefficient of resistance change with composition diminishes. The speed of response was relatively fast, with 80% signal change being attained within 60s. Reversal of the resistance change on removal of $O_2$ has been demonstrated.

Example 2

Figure 12:
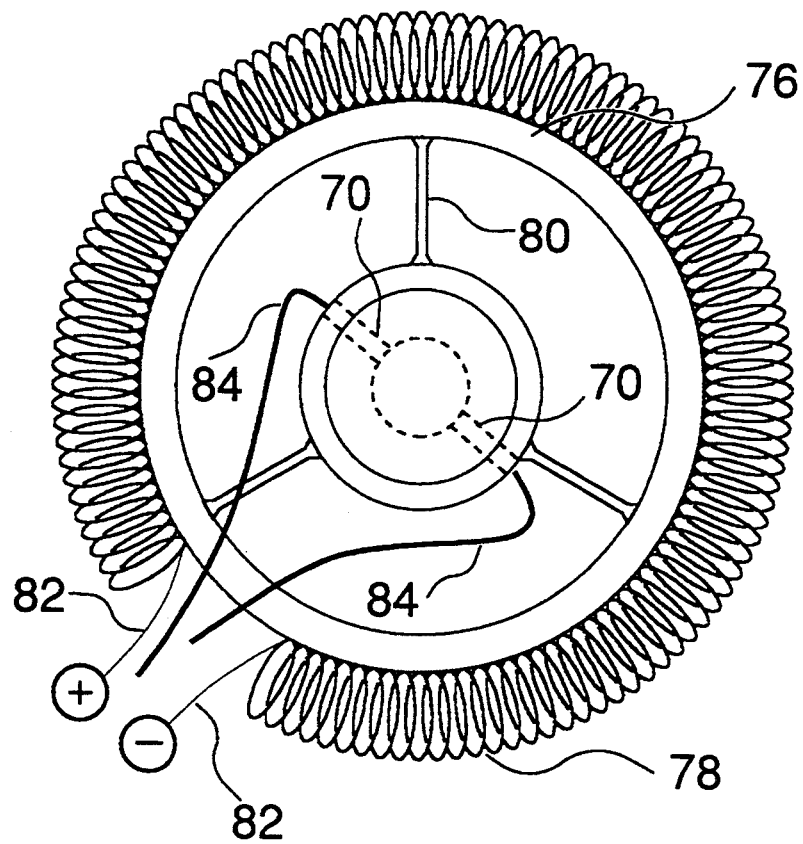
FIG. 12 illustrates an apparatus for bulk acoustic wave measurement.
Figure 12A:
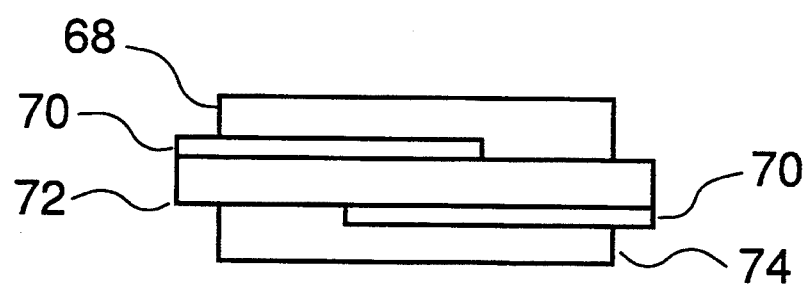
FIG. 12a is an enlargement of a portion of the apparatus of FIG. 12 indicated with phantom lines.

The $SrFeO_{2.5+x}$ film is deposited upon a piezoelectric (AT cut) quartz substrate which has evaporated gold electrodes on its surface for its electrical connection to an oscillation circuit. The apparatus for making the bulk acoustic wave measurement is similar in principle to the quartz crystal microbalance of Guilbault, [G. G. Guilbault and J. M. Jordan, CRC Critical Reviews 19, 1, (1988)]. The nominal frequency of the quartz crystal is 9 MHz. The assembly is shown in FIG. 12 and FIG. 12a, where the sensor layer 68 is deposited on the AT cut quartz 72, with gold electrodes 70 connected to a frequency measurement circuit through 84. This assembly is mounted by supports 80 in a ceramic tube 76 with a heater 78 and power supply connections 82. The film is 300 nm in thickness, and of mass 200 μg. On reaction with $O_2$ at 520 K., the mass change between the oxygen rich and deficient compositions is 4.4%, or 8.8 μg, the coefficient of frequency change with mass change of the film upon the oscillator surface is 1 Hz per 18 ng. Oxygen uptake occurs and the consequent mass change is expected to be linear with change in x. Hence the correlation between oxygen gas composition and sensor response (ie. frequency shift) is measured by monitoring the frequency change which occurs in the oscillator circuit.

Example 3

Figure 13:
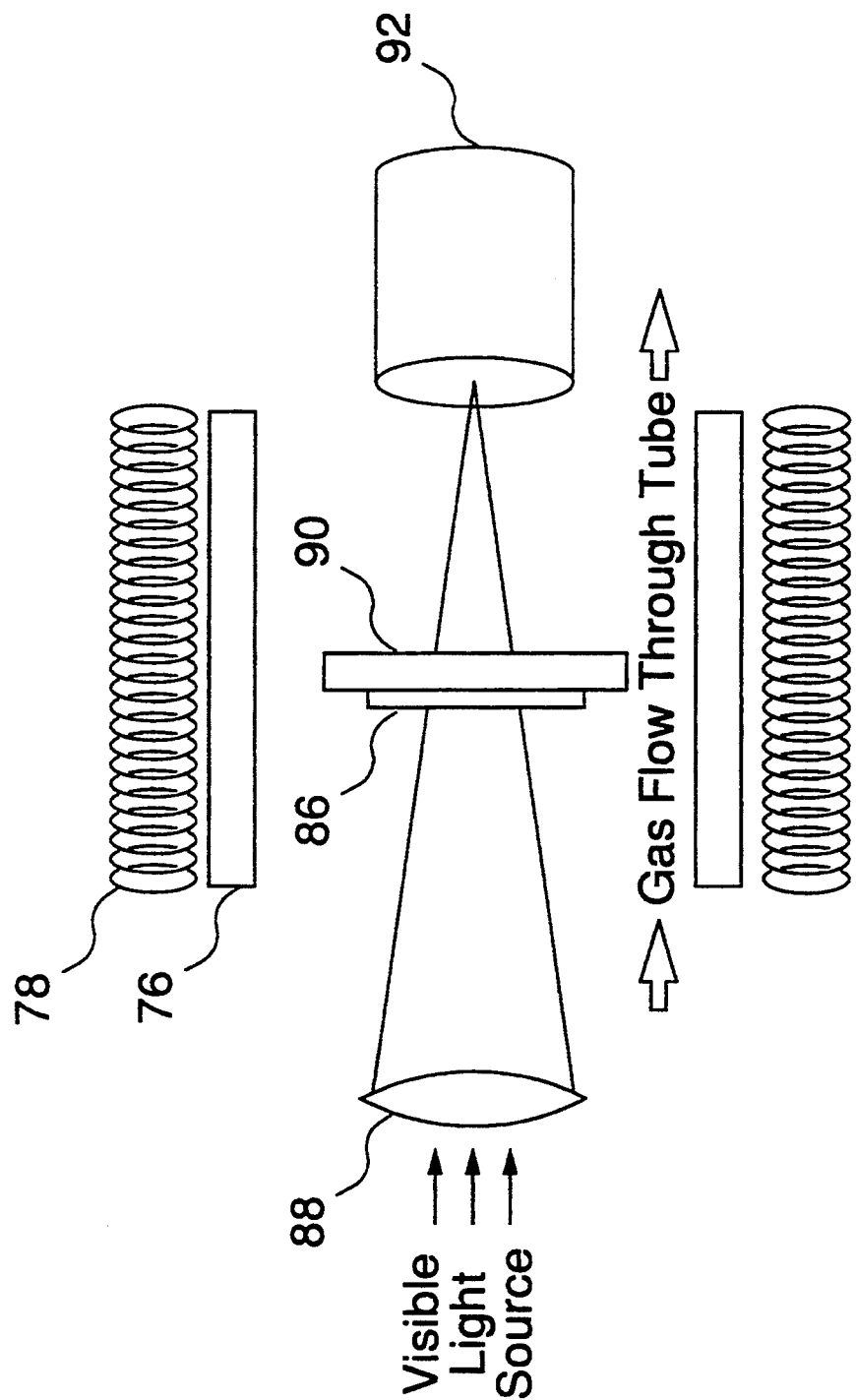
FIG. 13 is an apparatus for measuring optical transmissivity of a thin film of the invention on a transparent substrate.

A 100 nm film of $Sr_{0.9}La_{0.1}FeO_{2.5+x}$ 86 is deposited upon an optically polished quartz substrate 90 and mounted in an assembly as shown in FIG. 13. The substrate is mounted within a ceramic tube 76, heated to 670 K. by an external resistance heater 78 with a 30 W power supply, and the $N_2/O_2$ gas stream is passed over the film at a rate of 50 ml.min$^{-1}$. Radiation of $\lambda = 450$ nm is incident, via a lens 88, upon the film and the quantity which is transmitted through the film and substrate is monitored with a diode array detector 92. On exposure to oxygen the film composition changes, which results in a change in optical density due to the bulk uptake of oxygen. The consequent change in transmittance is correlated with the $O_2$ composition of $N_2/O_2$ gas stream. This is shown by FIG. 7 where the diminishing transmittance with increasing x, is clearly evident. It will be appreciated that the above embodiments of the invention are merely exemplary. More variations and modifications may occur to those skilled in the art and all such modifications are intended to fall within the scope of the invention as defined in the appended claims.

TABLE 1

X-RAY DIFFRACTION SPECTRA (Cu—K$_\alpha$)

| SrFeO$_{2.5}$ H179 | SrFe$_{0.9}$Ti$_{0.1}$O$_y$ H202 | SrFe$_{0.95}$V$_{0.05}$O$_y$ H210 | SrFe$_{0.9}$V$_{0.1}$O$_y$ H207 | SrFe$_{0.8}$V$_{0.2}$O$_y$ H211 | SrFe$_{0.9}$Cr$_{0.1}$O$_y$ H203 | SrFe$_{0.9}$Mn$_{0.1}$O$_y$ H196 | SrFe$_{0.9}$Co$_{0.1}$O$_y$ H197 | SrFe$_{0.9}$Ni$_{0.1}$O$_y$ H192 | SrFe$_{0.9}$Cu$_{0.1}$O$_y$ H191 | SrFe$_{0.8}$Cu$_{0.2}$O$_y$ H198 |
|---|---|---|---|---|---|---|---|---|---|---|
| 11.41 | 11.41 | 11.30 | | | | | 11.41 | 11.36 | 11.31 | 11.21 |
| 22.53 | 22.52 | | | | | | 22.54 | 22.64 | | |
| 23.26 | 23.27 | | 22.62 | 22.64 | | 22.76 | 23.28 | 23.26 | 22.65 | |
| 25.28 | 25.28 | | | | | | 25.31 | 25.36 | 23.23 | |
| | | | | | | | | | 25.32 | |
| 31.60 | 31.62 | | 28.84 | 28.90 | | | 31.66 | 31.73 | 31.75 | |
| 32.28 | 32.30 | 32.25 | 32.18 | 32.17 | | 31.77 | 32.30 | 32.26 | 32.22 | 32.19 |
| | | | 32.54 | | | 32.37 | | | | 32.46 |
| 32.82 | 32.85 | 32.73 | 32.72 | | | 32.85 | 32.79 | 32.90 | | 32.81 |
| | 34.49 | | | | | | 34.49 | | | |
| 39.35 | 39.34 | 39.94 | 39.67 | 39.66 | | 39.95 | 39.37 | 36.30 | 39.89 | 36.46 |
| 40.04 | 40.01 | | | | | | 40.06 | 40.08 | | 39.82 |
| 40.23 | 40.30 | | 41.33 | | | | 40.28 | 40.49 | | |
| 41.62 | 41.61 | 41.47 | 41.45 | | | 41.52 | 41.61 | 41.52 | 41.42 | 41.29 |
| | | | 43.50 | 43.53 | | | | | 41.66 | |
| 45.89 | 45.89 | 46.06 | 46.12 | 46.09 | | 46.10 | 45.93 | 46.10 | 45.98 | 45.90 |
| 46.67 | 46.57 | | 46.43 | 46.32 | | 46.41 | 46.61 | 46.36 | 46.17 | 46.43 |
| | | | 46.73 | | | 46.67 | | 46.67 | | |
| | | 46.92 | | | | 47.10 | | | | |
| 47.42 | 47.47 | | | 49.12 | | | 47.48 | 47.47 | 47.03 | 47.03 |
| 48.10 | 48.08 | | 48.99 | | | | 48.08 | 48.07 | | |
| 51.47 | 51.42 | | 51.91 | 51.87 | | | 51.54 | 51.61 | 51.78 | |
| 51.78 | 51.82 | | | | | | 51.87 | 51.94 | | |
| 56.64 | 56.66 | 56.89 | 56.87 | 56.81 | | 56.81 | 56.70 | 56.79 | 56.76 | 56.70 |
| | | 57.23 | 57.32 | 57.27 | | 57.30 | | | 57.24 | |
| 57.42 | 57.38 | 57.68 | 57.77 | 57.77 | | 57.72 | 57.41 | 57.24 | 57.66 | 57.58 |
| 57.71 | 57.69 | 57.99 | 58.08 | | | 58.59 | 57.75 | 57.86 | 58.51 | 58.51 |
| 62.14 | 62.14 | | | | | | 62.21 | | | |
| 63.13 | 63.14 | 63.95 | | | | | 63.16 | 63.21 | | |
| 64.19 | 64.15 | | | | | | 64.18 | 64.16 | 64.00 | 63.80 |
| 65.84 | 65.94 | 66.44 | 66.90 | | | | 65.96 | 66.25 | | |

TABLE 1-continued

X-RAY DIFFRACTION SPECTRA (Cu—Kα)

| SrFe₀.₇₅Cu₀.₂₅O_y H199 | SrFe₀.₇Cu₀.₃O_y H200 | SrFe₀.₆Cu₀.₄O_y H201 | Ca₀.₁Sr₀.₉FeO_y H204 | Ca₀.₂Sr₀.₈FeO_y H205 | La₀.₁Sr₀.₉FeO_y H206 | (h,k,l) b = brownmillerite p = perovskite |
|---|---|---|---|---|---|---|
| 11.25 | 11.36 | 11.36 | 11.47 | 11.55 | 11.38 | |
| 22.82 | 22.78 | 22.79 | 22.56 | 22.55 | 22.58 | p (1,0,0) |
| 23.16 | | | 23.35 | 23.44 | 23.28 | b (2,0,0) |
| | | | | 25.41 | 25.29 | p (1,1,0) |
| | | | 31.62 | 31.66 | 31.74 | b (1,4,1)-(0,0,2) |
| 32.20 | 32.01 | 31.93 | 32.39 | 32.52 | 32.24 | b (1,5,0) |
| | 32.38 | 32.41 | | | | |
| 32.84 | 32.69 | 32.72 | 32.93 | 33.10 | 32.45 | |
| 67.16 | 67.26 | | 67.19 | | | |
| 67.47 | 67.39 | 67.43 | 67.50 | 67.44 | 67.32 | |
| 67.80 | 67.72 | 67.74 | 67.93 | | 67.94 | |
| 68.80 | | | 68.66 | | | |
| 75.41 | | | 75.46 | | | |
| 76.19 | | | 76.26 | | | |
| 76.55 | 76.42 | 77.04 | 76.82 | 76.44 | 76.47 | |
| 76.73 | 76.51 | | 77.24 | | 76.91 | |
| 77.28 | | | 78.05 | | | |
| 78.05 | | | 80.03 | | | |
| 79.96 | 80.84 | | 79.97 | 79.97 | | |
| | 80.98 | | 80.10 | 80.10 | | |
| 81.30 | | | 81.37 | 81.59 | 81.90 | 82.17 |
| 81.92 | | | 81.99 | 81.95 | | |
| 82.58 | 85.29 | | 82.59 | 82.31 | | |
| 82.85 | 85.45 | 86.10 | 82.99 | 82.81 | | |
| 86.27 | | | 86.32 | 86.44 | | |
| 91.98 | 94.06 | 94.67 | 92.00 | | | |
| 94.64 | 94.49 | 94.95 | 94.64 | 94.52 | | 94.85 |
| 94.82 | | | 94.78 | 94.95 | | |
| 94.97 | 95.66 | | 95.11 | 95.17 | | 95.50 |
| | 96.16 | 96.67 | 96.14 | | | |
| 96.26 | | | 96.40 | | | |
| 96.38 | | | | | | |
| 103.6 | 103.0 | 113.1 | 103.7 | | | 102.1 |
| 118.6 | 112.3 | | 118.8 | | | |

(h,k,l) markers: b (1,0,0); p (1,0,0); b (2,0,0); p (1,1,0); b (1,4,1)-(0,0,2); b (1,5,0); b = brownmillerite, p = perovskite

TABLE 1-continued
X-RAY DIFFRACTION SPECTRA (Cu—Kα)

| | | | | | |
|---|---|---|---|---|---|
| 36.46 | 36.51 | 36.50 | | 36.26 | |
| 37.71 | 37.72 | 37.71 | | | |
| 37.37 | 37.91 | 37.96 | | | |
| 39.38 | | | | | |
| 39.80 | 39.94 | 39.97 | 39.42 | 39.53 | 34.45 b (2,4,0) |
| | | | | | p (1,1,1) |
| 41.33 | 41.39 | 41.48 | | 40.28 | 39.98 b (0,4,2) |
| 41.63 | 41.59 | 41.65 | 40.13 | 40.49 | 40.30 |
| 42.56 | 42.40 | 42.37 | 41.76 | 41.95 | 41.51 b (1,6,1) |
| 45.90 | 46.01 | | 45.93 | 46.02 | 45.99 b (2,0,2) |
| 46.46 | 46.47 | 46.48 | | | |
| 46.64 | | | 46.90 | 47.19 | 46.39 b (0,8,0)-(1,5,2) |
| | | | | | p (2,0,0) |
| | | | 47.48 | 47.58 | 47.49 b (2,2,2)-(2,6,0) |
| | | | 48.21 | 48.50 | 47.98 b (0,6,2) |
| 49.88 | | | | | |
| | | | 51.51 | 51.62 | 51.64 |
| | | | | | 51.90 |
| | 52.26 | 52.31 | | | |
| 56.84 | | | 56.70 | 56.85 | 56.79 b (3,4,1) |
| 57.35 | | | | | |
| 57.65 | 57.72 | 57.74 | 57.83 | 57.26 | 57.32 b (2,8,0) |
| | | | | 57.96 | 57.69 b (1,4,3) |
| 63.84 | | | 62.22 | 62.35 | |
| | | 64.10 | 63.20 | 63.41 | 63.20 p (2,1,1) |
| | | | 64.33 | 64.52 | 64.02 |
| | | | 65.91 | 66.08 | 66.19 |
| | | | 67.24 | 67.28 | |
| 67.13 | | | 67.70 | 67.43 | 67.41 |
| 67.90 | 67.73 | 67.79 | 67.96 | 68.02 | 67.90 p (2,2,0) |
| | | | 75.41 | 75.47 | |
| | | | 76.34 | 76.50 | 76.35 p (3,1,0) |
| 77.05 | 77.09 | 77.14 | 76.79 | 76.97 | 76.82 |
| | | | | 77.09 | 77.15 |
| | | | | 78.11 | 77.87 |
| | | | 80.03 | 80.21 | |
| | | | | 81.67 | 81.95 p (3,1,1) |
| 82.22 | | | 82.13 | 82.27 | 82.69 |

TABLE 1-continued

X-RAY DIFFRACTION SPECTRA (Cu—K$_\alpha$)

| | | | | |
|---|---|---|---|---|
| 85.81 | | 86.12 | 86.92 | |
| | 94.64 | | 92.63 | 86.18 p (2,2,2) |
| 94.55 | 94.90 | 95.02 | | |
| 94.88 | | | | 94.71 |
| | | | | 94.99 |
| 95.33 | 95.18 | | 95.44 | p (3,2,1) |
| 101.9 | 113.6 | 113.4 | | |

TABLE 2
STOICHIOMETRIC INCREASE IN OXYGEN DUE TO COOLDOWN PROCESS

| Compound | | 250° C. | 150° C. | 100° C. | 25° C. | Δx 250° C.→25° C. |
|---|---|---|---|---|---|---|
| SrFe0.9Ti0.1Oy+x | pressure (torr) | 1233 | 1185 | 1169 | 1137 | 0.053 |
| | stoich (x) | 0.372 | 0.411 | 0.422 | 0.425 | |
| SrFe0.95V0.5Oy+x | pressure (torr) | 1216 | 1190 | 1174 | 1147 | 0.002* |
| | stoich (x) | 0.371 | 0.372 | 0.372 | 0.373 | |
| SrFe0.9V0.1Oy+x | pressure (torr) | 1153 | 1123 | 1111 | 1081 | 0.019* |
| | stoich (X) | 0.278 | 0.285 | 0.285 | 0.297 | |
| SrFe0.8V0.2Oy+x | pressure (torr) | 1182 | 1162 | 1150 | 1121 | 0.001* |
| | stoich (X) | 0.198 | 0.199 | 0.199 | 0.199 | |
| SrFe0.9Cr0.1Oy+x | pressure (torr) | 1194 | 1171 | 1159 | 1133 | 0.007* |
| | stoich (x) | 0.321 | 0.316 | 0.315 | 0.314 | |
| SrFe0.9Mn0.1Oy+x | pressure (torr) | 1295 | 1245 | 1227 | 1198 | 0.042 |
| | stoich (x) | 0.386 | 0.427 | 0.428 | 0.428 | |
| SrFe0.9Co0.1Oy+x | pressure (torr) | 1192 | 1138 | 1120 | 1092 | 0.063 |
| | stoich (x) | 0.421 | 0.472 | 0.478 | 0.484 | |
| SrFe0.9Ni0.1Oy+x | pressure (torr) | 1265 | 1207 | 11840 | 1153 | 0.075 |
| | stoich (x) | 0.409 | 0.464 | 0.476 | 0.484 | |
| SrFe0.9Cu0.1Oy+x | pressure (torr) | 1251 | 1203 | 1185 | 1154 | 0.069 |
| | stoich (x) | 0.410 | 0.467 | 0.469 | 0.479 | |
| SrFe0.8Cu0.2Oy+x | pressure (torr) | 10678 | 1021 | 1009 | 982 | 0.026 |
| | stoich (x) | 0.361 | 0.381 | 0.381 | 0.387 | |
| SrFe0.75Cu0.25Oy+x | pressure (torr) | 1158 | 1120 | 1105 | 1078 | 0.021 |
| | stoich (x) | 0.314 | 0.330 | 0.331 | 0.335 | |
| SrFe0.7Cu0.3Oy+x | pressure (torr) | 1211 | 1182 | 1165 | 1136 | 0.014* |
| | stoich (x) | 0.265 | 0.268 | 0.271 | 0.279 | |
| SrFe0.6Cu0.4Oy+x | pressure (torr) | 1112 | 1086 | 1072 | 1042 | 0.007* |
| | stoich (x) | 0.228 | 0.230 | 0.230 | 0.235 | |
| Ca0.1Sr0.9FeOy+x | pressure (torr) | 1192 | 1142 | 1122 | 1089 | 0.050 |
| | stoich (x) | 0.407 | 0.443 | 0.452 | 0.457 | |
| Ca0.2Sr0.8FeOy+x | pressure (torr) | 1251.86 | 1203.61 | 1182.30 | 1152.10 | 0.053 |
| | stoich (x) | 0.393 | 0.429 | 0.440 | 0.446 | |
| La0.1Sr0.9FeOy+x | pressure (torr) | 1191 | 1158 | 1139 | 1110 | 0.027 |
| | stoich (x) | 0.408 | 0.424 | 0.427 | 0.435 | |

*Δx values marked by asterisk indicate analogs for which stoichiometric increases are minimal.

I claim:

1. An oxygen sensor comprising:
a thermally stable and chemically stable substrate,
a thin uniform crystalline film of a nonstoichiometric compound oxide of the general formula $ABO_{2.5+x}$ supported on the substrate, wherein A is an element of the lanthanum family, an alkaline earth metal or a mixture thereof, B is a transition metal or a mixture of transition metals, and x is a number which defines bulk oxygen stoichiometry of the oxide and is variable between about 0 for an oxygen deplete and less than 0.5 for an oxygen saturated crystalline phase of the compound oxide, the film being of a thickness such that the compound oxide can undergo reversible bulk reaction with oxygen at an elevated temperature in an oxygen-containing atmosphere thereby undergoing a transition between the oxygen saturated and oxygen-deplete crystalline phases, and
a detecting means for detecting a change in physical properties of said film, said change being a function of the varying bulk oxygen stoichiometry of the film.

2. The sensor as defined in claim 1 wherein the thickness of the layer is such that an optical transmittance of the layer varies depending on the value of x.

3. The sensor as defined in claim 2 wherein said detecting means is an optical transmittance detecting means.

4. The sensor as defined in claim 1 wherein said detecting means is a weight detecting means.

5. The sensor according to claim 1 wherein said detecting means is a bulk electrical resistance detecting means.

6. The sensor according to claim 1 wherein the film has a surface area in the order of that of an epitaxial film.

7. The sensor according to claim 4 wherein the weight detecting means is a quartz crystal microbalance.

8. The sensor according to claim 1 wherein the substrate is sapphire.

9. The sensor according to claim 8 wherein a thin film of cerium oxide is interposed between the substrate and the compound oxide film.

10. The sensor according to claim 1 wherein A is strontium (Sr) and B is iron (Fe).

11. A method of making an oxygen sensor, comprising
providing a thermally stable and chemically stable substrate,
applying onto the substrate in an oxygen-controlled atmosphere a uniform crystalline thin film of a non-stoichiometric compound oxide of the general formula $ABO_{2.5+x}$, wherein A is an element of the lanthanum family, an alkaline earth metal or a mixture thereof, B is a transition metal or a mixture of transition metals, and x is a number which is variable between 0 for an oxygen deplete and less than 0.5 for an oxygen saturated crystalline phase of the compound oxide, the layer being of a thickness such that the compound oxide can undergo reversible bulk reaction with oxygen at an elevated temperature in an oxygen-containing atmosphere thereby undergoing transition between the oxygen saturated and oxygen-deplete crystalline phases, and providing a detecting means in association with the thin film for detecting a change in physical properties of said film.

12. The method of claim 11 wherein a thin film of cerium dioxide is applied onto the substrate before the film of said compound oxide is applied thereon.

13. The method according to claim 11 wherein the substrate is a transparent material selected from sapphire, quartz and AT cut quartz.

14. The method according to claim 11 wherein the film is applied by means of pulsed laser ablation.

* * * * *